US008105533B2

(12) United States Patent
Hisamatsu et al.

(10) Patent No.: US 8,105,533 B2
(45) Date of Patent: Jan. 31, 2012

(54) APPARATUS FOR MEASURING CORROSION LOSS

(75) Inventors: Tohru Hisamatsu, Yokosuka (JP); Isao Yuri, Yokosuka (JP)

(73) Assignee: Central Research Institute of Electric Power Industry, Tokyo (JP)

( * ) Notice: Subject to any disclaimer, the term of this patent is extended or adjusted under 35 U.S.C. 154(b) by 1646 days.

(21) Appl. No.: 11/216,059

(22) Filed: Sep. 1, 2005

(65) Prior Publication Data
US 2006/0045166 A1    Mar. 2, 2006

(30) Foreign Application Priority Data
Sep. 2, 2004 (JP) .................................. 2004-256211

(51) Int. Cl.
*G01N 31/00* (2006.01)
(52) U.S. Cl. ............................. 422/53; 436/6; 73/865.6
(58) Field of Classification Search ........ 436/6; 422/53; 73/865.6
See application file for complete search history.

(56) References Cited

U.S. PATENT DOCUMENTS

| | | | | |
|---|---|---|---|---|
| 3,488,681 A | * | 1/1970 | Mita et al. ....................... | 374/57 |
| 5,254,318 A | * | 10/1993 | Williams et al. ............... | 422/197 |
| 6,536,089 B1 | * | 3/2003 | Komiya et al. ............... | 29/455.1 |

FOREIGN PATENT DOCUMENTS

| | | |
|---|---|---|
| JP | 3-229133 | 10/1991 |
| JP | 6-151414 A | 5/1994 |
| JP | 10-185799 | 7/1998 |
| JP | 2001-345314 A | 12/2001 |
| JP | 2002-277054 A | 9/2002 |
| JP | 2003-315253 | 11/2003 |

\* cited by examiner

*Primary Examiner* — Lyle Alexander
(74) *Attorney, Agent, or Firm* — Sughrue Mion, PLLC

(57) ABSTRACT

The present invention provides a corrosion loss measuring apparatus which enables to quantitatively determine corrosion loss characteristics of ceramic materials and heat-resistant metallic materials, which is excellent in terms of safety, cost, and operation easiness, and whose size can be reduced. The invention also provides a method for measuring corrosion loss by use of the apparatus. The corrosion loss measuring apparatus which, in use, allows an atmosphere gas to be continuously fed into a test-piece-placing section for accommodating a material test piece, the atmosphere gas having a predetermined composition and having been heated to a predetermined temperature, wherein the apparatus includes a gas-heating section and a test-piece-placing section, the gas-heating section and the test-piece-placing section are included a one-piece ceramic-made tube for use in a heating furnace, and the cross-sectional area of the gas-heating section through which the gas flows is larger than that of the test-piece-placing section.

18 Claims, 3 Drawing Sheets

APPARATUS FOR MEASURING CORROSION LOSS

BACKGROUND OF THE INVENTION

1. Field of the Invention

The present invention relates to an apparatus for measuring corrosion loss (hereinafter referred to as a corrosion loss measuring apparatus) and to a method for measuring corrosion loss. More particularly, the invention relates to a corrosion loss measuring apparatus for measuring corrosion loss of test pieces formed of a variety of heat-resistant materials such as ceramics and heat-resistant metals under high-temperature gas flow, and to a method for measuring corrosion loss by use of the apparatus.

2. Background Art

In the field of flow of high-temperature combustion gas exceeding 1,000° C. (such situation is found in, for example, a gas turbine), some heat-resistant materials are known to be deteriorated by a combustion gas component. Recent studies have revealed that even a ceramic material (a material having excellent heat resistance) is gradually corroded to lose volume with elapse of time under the flow of combustion gas. One possible reason for the corrosion loss is that steam contained in the combustion gas reacts with the ceramic material to form a hydroxide, and vaporization of the formed hydroxide is promoted by the gas flow, thereby removing a portion of the ceramic material. Therefore, a ceramic material for use in high-temperature (>1,000° C.) combustion gas must be quantitatively assessed in terms of corrosion loss after use for a predetermined period of time, and a simple technique for predicting the corrosion loss amount is demanded.

In order to experimentally induce corrosion loss of a ceramic material, the following three conditions must be satisfied simultaneously. That is, the material is maintained at high temperature higher than about 1,000° C.; the atmosphere gas surrounding the material contains steam; and the material is placed under flow of the atmosphere gas. Notably, the amount of corrosion loss of the material is known to increase with material temperature, partial pressure of steam contained in the atmosphere gas, and gas flow rate.

Conventionally, a combustion-gas-flow-type corrosion loss measuring apparatus is employed for inducing corrosion loss of a ceramic material and quantitatively assessing corrosion loss characteristics of the material. The apparatus is employed in combination with a combustion gas generator such as a burner or a gas turbine combustion apparatus, and a test piece is placed under combustion gas flow. Some types of such combustion-gas-flow-type corrosion loss measuring apparatuses allow independent control of temperature, gas composition, gas flow rate, and gas pressure. However, the above combustion-gas-flow-type corrosion loss measuring apparatuses have drawbacks; e.g., safety is not assured due to combustion of a large amount of fuel; the apparatuses are large-scale and have a complex structure, leading to high cost and mal-operability; and impurities (oxide of a metal member exposed at high temperature, corroded material formed on/in the piping, etc.) contained in combustion gas are deposited on the material test piece. Thus, a limitation is placed on the precision of measurement. In addition, the gas composition can be varied only within a narrow range, and maximum gas temperature is generally limited to about 1,500° C.

Another conventionally employed apparatus is an electric-furnace-type corrosion loss measuring apparatus in which a test piece is placed in a furnace that is electrically heated to high temperature and an atmosphere gas containing steam and simulating combustion gas is introduced into the furnace. As compared with a combustion-gas-flow-type corrosion loss measuring apparatus, the electric-furnace-type corrosion loss measuring apparatus is smaller, is of low cost, is easily operated, and assures high-safety. In addition, the gas composition can be varied over a wide range, and the gas temperature can be readily elevated to about 1,700° C., which are advantageous. However, the composition-regulated atmosphere gas is fed directly into the electric furnace in which the test piece is placed, and a large amount of atmosphere gas must be supplied in order to elevate gas flow rate, resulting in lowering of temperature inside the electric furnace. Therefore, the gas flow rate is required to be limited to some cm/s or less. Under such flow conditions, corrosion loss of the test piece cannot be induced, or even if corrosion occurs, only a small amount of corrosion loss is induced. As a result, it is considerably difficult to quantitatively assess corrosion loss when an electric-furnace-type corrosion loss measuring apparatus is employed.

Meanwhile, in relation to a semiconductor device production apparatus, there have been proposed heating apparatuses for heating, to a predetermined temperature, a gas to be fed to a high-temperature furnace for processing a semiconductor, each heating apparatus being provided so as to heat a conduit for feeding the gas to the furnace. These apparatuses are disclosed in Japanese Application Laid-Open (kokai) Nos. 6-151414, 2001-345314, 2002-277054, etc. Since each of the disclosed heating apparatuses is provided separately from the high-temperature furnace, the heated gas is fed to the high-temperature furnace through a conduit connected to the furnace. Since the gas to be fed to a semiconductor device production device is required to be heated to about 1,000° C., a heating tube or a conduit for feeding the gas supplied from the heating tube may be formed of quartz glass or a similar material.

In the case where a corrosion loss measuring apparatus is employed for inducing corrosion loss of a ceramic material and quantitatively and effectively assessing corrosion loss characteristics of the material, the atmosphere gas is required to be heated to about 1,700° C. Therefore, a heating tube and filler for use in a heating apparatus, as well as a conduit for feeding heated gas, cannot be formed from quartz glass, which is softened at about 1,400° C. A translucent ceramic material such as translucent polycrystalline alumina is an alternative, but the translucent ceramic material is highly expensive. Thus, non-translucent ceramic material such as alumina or zirconia is employed as a material for providing a heating apparatus for attaining a gas temperature of 1,700° C., a heating tube and filler for use in the heating apparatus, and a conduit for feeding heated gas.

When a heating tube and fillers therefore formed of a non-translucent ceramic material are employed, the heat generated from the heating medium is transferred through the inner wall of the heating tube and converted to radiation. The atmosphere gas is effectively heated upon passage through radiated fillers. However, the portion where the gas can be effectively heated is limited to a zone in the vicinity of the inner wall of the heating tube. Thus, when a large amount of gas is fed to the heating tube, a wide temperature distribution profile (i.e., a large difference in temperature) is observed in a cross-sectional area through which the gas flows. When such a temperature distribution profile is observed, reliability of the measured data is considerably affected, and the mean gas temperature at the outlet of the heating tube is lowered. In order to overcome these drawbacks, the heating apparatus must be scaled up, which is problematic. When the measuring furnace in which a test piece is placed is connected with the heating apparatus via a ceramic gas conduit, connection between ceramic parts and sealing the gas in the connection portions become difficult.

Thus, according to conventional techniques, there has not been attained a material corrosion loss measuring apparatus which can induce corrosion loss of a ceramic material through electrical heating and quantitatively and effectively assess corrosion loss characteristics of the material.

As described above, according to the conventional techniques, corrosion loss characteristics of ceramic materials and heat-resistant metallic materials have been evaluated solely by use of a combustion-gas-flow-type corrosion loss measuring apparatus in combination with a combustion gas generator, but unsolved problems in terms of safety, cost, operability, etc. have remained. One candidate apparatus for solving the problems is an electric heating material measuring apparatus. The temperature required for carrying out corrosion loss measurement is about 1,000 to 1,700° C. for ceramic material, and about 800 to 1,200° C. for heat-resistant metallic material. Therefore, the apparatus must employ a ceramic member at high-temperature portions. As a result, in the electric-heating-type measuring apparatus, a large amount of gas cannot be heated effectively and uniformly to about 1,700° C., and sealing of ceramic members for preventing leakage of gas is difficult to attain.

SUMMARY OF THE INVENTION

The present invention was conceived in an attempt to solve the aforementioned problems. Thus, an object of the present invention is to provide a corrosion loss measuring apparatus which can quantitatively determine corrosion loss characteristics of ceramic materials and heat-resistant metallic (alloy) materials, which is excellent in terms of safety, cost, and easiness of operation, and whose size can be reduced. Another object of the invention is to provide a method for measuring corrosion loss by use of the apparatus.

The present inventors have carried out extensive studies in order to attain the aforementioned objects, and have found that the objects can be attained through employment of a one-piece ceramic tube including a gas-heating section and a test-piece-placing section for use in a heating furnace, in which a cross-sectional area of the gas-heating section through which the gas flows larger than that of the test-piece-placing section. The present invention has been accomplished on the basis of this finding.

Accordingly, in one aspect of the present invention, there is provided a corrosion loss measuring apparatus which, during use, allows an atmosphere gas to be continuously fed into a test-piece-placing section for accommodating a material test piece, the atmosphere gas having a predetermined composition and having been heated to a predetermined temperature, wherein the apparatus comprises a gas-heating section and a test-piece-placing section, the gas-heating section and the test-piece-placing section are included in a one-piece ceramic tube for use in a heating furnace, and the cross-sectional area of the gas-heating section through which the gas flows is larger than that of the test-piece-placing section.

In another aspect of the invention, there is provided a method for measuring corrosion loss comprising measuring corrosion loss by use of the above corrosion loss measuring apparatus, wherein the gas-heating section and the test-piece-placing section have a portion to be in contact with a gas which is formed of a ceramic material which is free from any component element (excluding oxygen) of the material test piece.

BRIEF DESCRIPTION OF THE DRAWINGS

Various other objects, features, and many of the attendant advantages of the present invention will be readily appreciated as the same becomes better understood with reference to the following detailed description of the preferred embodiments when considered in connection with the accompanying drawings, in which.

DETAILED DESCRIPTION OF PREFERRED EMBODIMENTS

Figure 1A:
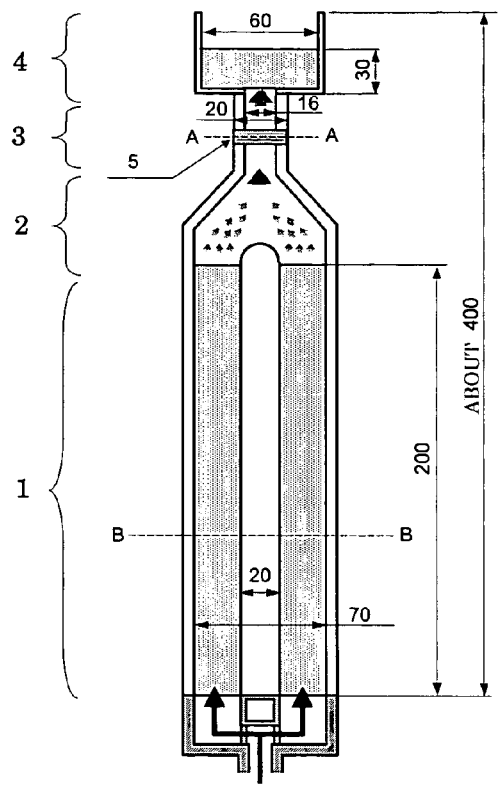
FIGS. 1A to 1D schematically show the corrosion loss measuring apparatus of the present invention.

During use, the corrosion loss measuring apparatus of the present invention allows an atmosphere gas to be continuously fed into a test-piece-placing section for accommodating a material test piece, the atmosphere gas having a predetermined composition and having been heated to a predetermined temperature, wherein the apparatus comprises a gas-heating section and a test-piece-placing section, and the gas-heating section and the test-piece-placing section are included in a one-piece ceramic tube for use in a heating furnace. Therefore, use of an optional gas flow path for connecting the gas-heating section with the test-piece-placing section is not required, thereby eliminating heat loss in the conduit and facilitating sealing of the members for preventing leakage of gas.

In the corrosion loss measuring apparatus of the present invention, preferably, a ceramic tube having one closed end is provided along the center axis of the gas flow path in the gas-heating section and in parallel to the gas flow direction, thereby forming a double-wall tube gas-heating section; the space between the outer tube and the inner tube serves as a gas flow path; and a ceramic heat-transfer promoter having gas permeability is charged in the gas flow path. Through employment of the structure, a portion in the vicinity of the inner surface of the outer tube, where radiation from the heated outer tube and thermally conducted heat are effectively transferred to the gas by the mediation of the heat transfer promoter, can be exclusively employed as a gas flow path. Therefore, a uniform gas temperature distribution in a cross-section through which gas flows (i.e., minimization of temperature difference) can be attained. In this embodiment, a heater may be placed either outside the outer tube or inside the inner tube. Alternatively, heaters may be placed both outside the outer tube and inside the inner tube:

In the corrosion loss measuring apparatus of the present invention, preferably, a plurality of ceramic inner tubes, each having a closed end and containing a heating medium inserted therein, are provided in parallel to the gas flow direction in a gas flow path of the gas-heating section; and a ceramic heat-transfer promoter having gas permeability is charged in a gas flow path defined by the outer tube and the inner tubes. In this embodiment, heaters may be placed outside the outer tube and/or inside at least one of the inner tubes. Needless to say, heaters may be placed both outside the outer tube and inside all the inner tubes. Through employment of the structure, uniformity in gas temperature distribution in a cross-section through which gas flows is enhanced.

According to the corrosion loss measuring apparatus of the present invention, a cross-sectional area of the gas-heating section through which gas flows is larger than that of the test-piece-placing section. Thus, a large amount of gas can be heated sufficiently, and the gas flow rate in the test-piece-placing section can be increased, whereby a test piece undergoes corrosion loss. Since a cross-sectional area of the gas-heating section through which gas flows is larger than that of the test-piece-placing section, a flow-limiting section for gradually reducing the cross-sectional area through which gas flows may be provided between the outlet of the gas-heating section and the inlet of the test-piece-placing section. Alternatively, the outlet of the gas-heating section is made of a wall (plate) having an opening, and the inlet of the test-piece-placing section having the same cross-sectional area is connected through the opening. Among these modes, provision of a flow-limiting section for gradually reducing the cross-sectional area through which gas flows is preferred for uniformly feeding, to the test-piece-placing section, the heated gas coming from any of the gas flow paths in the gas-heating section.

In the corrosion loss measuring apparatus of the present invention, no particular limitation is imposed on the shape and structure of the test-piece-placing section, on the shape, structure, and other properties of the material test piece to be placed in the section, or on the method for sustaining the material test piece, so long as the material test piece is placed under the heated atmosphere gas flow. For example, the entirety of a material test piece (excluding a holding portion) may be placed under gas flow. Alternatively, a test piece (cylinder-form, ring-form, plate-form, etc.) may be placed on the entirety or a portion of the inner wall of the gas flow path in the test-piece-placing section, and the gas flows on the surface of the test piece. Two or more test pieces formed from different materials may be placed simultaneously in the test-piece-placing section. The method for supporting a test piece is not particularly limited. For example, holes through which the test piece can be inserted are provided in the surface of the test-piece-placing section, the holes opposing each other, and the test piece is inserted through the holes and supported. Alternatively, holes through which a pin can be inserted are provided in the surface of the test-piece-placing section, the holes opposing each other, and a pin is inserted through the holes for supporting the test piece. Yet alternatively, in the test-piece-placing section of a hollow cylinder, a portion having a greater diameter may be provided, and a ring-form test piece is supported through insertion in the portion, while the inner surface of the test-piece-placing section is leveled.

In the corrosion loss measuring apparatus of the present invention, preferably, the cross-sectional area through which the gas flows on the downstream side of the gas outlet of the test-piece-placing section is larger than that of the test-piece-placing section; a ceramic radiation shield is provided in the gas flow path on the downstream side of the gas outlet of the test-piece-placing section; and the gas-heating section, the test-piece-placing section, and the radiation shield are placed in a heating furnace. By controlling the cross-sectional area through which the gas flows on the downstream side of the gas outlet of the test-piece-placing section to exceed that of the test-piece-placing section, gas flow rate on the downstream side of the gas outlet of the test-piece-placing section is reduced to thereby reduce pressure loss, whereby an increase in pressure inside the gas flow path of the corrosion loss measuring apparatus can be prevented. As a result, sealing of the ceramic tube is facilitated. In addition, through provision of the ceramic radiation shield in the gas flow path on the downstream side of the gas outlet of the test-piece-placing section, the temperature at the gas outlet opening of the test-piece-placing section, which is ready to cool, can be maintained at a predetermined temperature, and temperature drop of the test piece due to radiation-related heat loss can be prevented.

The corrosion loss measuring apparatus of the present invention employs a ceramic tube and may further include a ceramic heat-transfer promoter and a ceramic radiation shield. These ceramic members may be formed from an oxide ceramic material that is remarkably resistive to corrosion loss (e.g., $ZrO_2$, $HfO_2$, or a mixture thereof) or a complex oxide ceramic material that is resistive to corrosion loss (e.g., $Y_2SiO_5$, $Yb_2Si_2O_7$, or $Lu_2Si_2O_7$). Among these, oxide ceramic materials such as $ZrO_2$, $HfO_2$, and a mixture thereof (total amount of $SiO_2$ and $Al_2O_3$ as impurities: 1% or less) are particularly preferred. The aforementioned ceramic tube, ceramic heat-transfer promoter, ceramic radiation shield, or a similar ceramic member may be made of a ceramic material in its entirety. Alternatively, at least a surface portion of each member, which portion is to be contact with an atmosphere gas, may be made of a ceramic material. Specifically, a heat-resistant substrate coated with the ceramic material may be used. The entire surface of the substrate may be coated with the ceramic material, or it may be the case that only a surface portion to be contact with an atmosphere gas is coated with the ceramic material. Through employment of such ceramic members, corrosion loss of the members employed in the gas flow path can be prevented.

The method for measuring corrosion loss of the present invention is carried out by use of the aforementioned corrosion loss measuring apparatus. The portion of the apparatus which extends from the gas-heating section to the test-piece-placing section and which is to be in contact with a gas is preferably formed of a ceramic material that is free from any component element (excluding oxygen) of the material test piece. For example, when the material test piece is $Al_2O_3$, the gas-contact portion is preferably formed of an oxide ceramic material or a complex oxide ceramic material containing no Al (e.g., $ZrO_2$ or $HfO_2$), whereas when the material test piece is $ZrO_2$, the gas-contact portion is preferably formed an oxide ceramic material or a complex oxide ceramic material containing no Zr (e.g., $Al_2O_3$). Through employment of such a ceramic portion, corrosion loss of the test piece can be measured with high precision. This is because, even though the ceramic member forming the gas flow path undergoes corrosion loss through reaction with steam, the reaction product is a species different from the product formed through reaction of the test piece and steam, and measurement of corrosion loss of the test piece is not affected.

In the method for measuring corrosion loss of the present invention carried out by use of the aforementioned corrosion loss measuring apparatus, the average temperature of the gas that flows through the gas flow path is preferably controlled to fall within a range of 1,000° C. to 1,700° C.

An embodiment of the corrosion loss measuring apparatus and an exemplary mode for carrying out the method for measuring corrosion loss of the present invention will next be described with reference to the attached drawings.

Figure 1B:
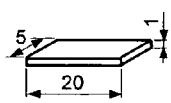
Figure 1C:
Figure 1D:
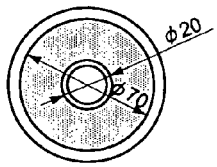

FIGS. 1A to 1D schematically show the corrosion loss measuring apparatus of the present invention. FIG. 1A shows the overall structure of the corrosion loss measuring apparatus of the present invention. In FIG. 1A, reference numerals 1, 2, 3, and 4 denote a gas-heating section, a flow-limiting section, a test-piece-placing section, and a gas-discharging section, respectively. The apparatus has an overall length of about 400 mm. FIG. 1B shows the shape and dimensions (unit: mm) of a material test piece. FIG. 1C is a cross-section of the apparatus, cut along line A-A in FIG. 1A, and FIG. 1D is a cross-section of the apparatus, cut along line B-B in FIG. 1A.

Figure 2:
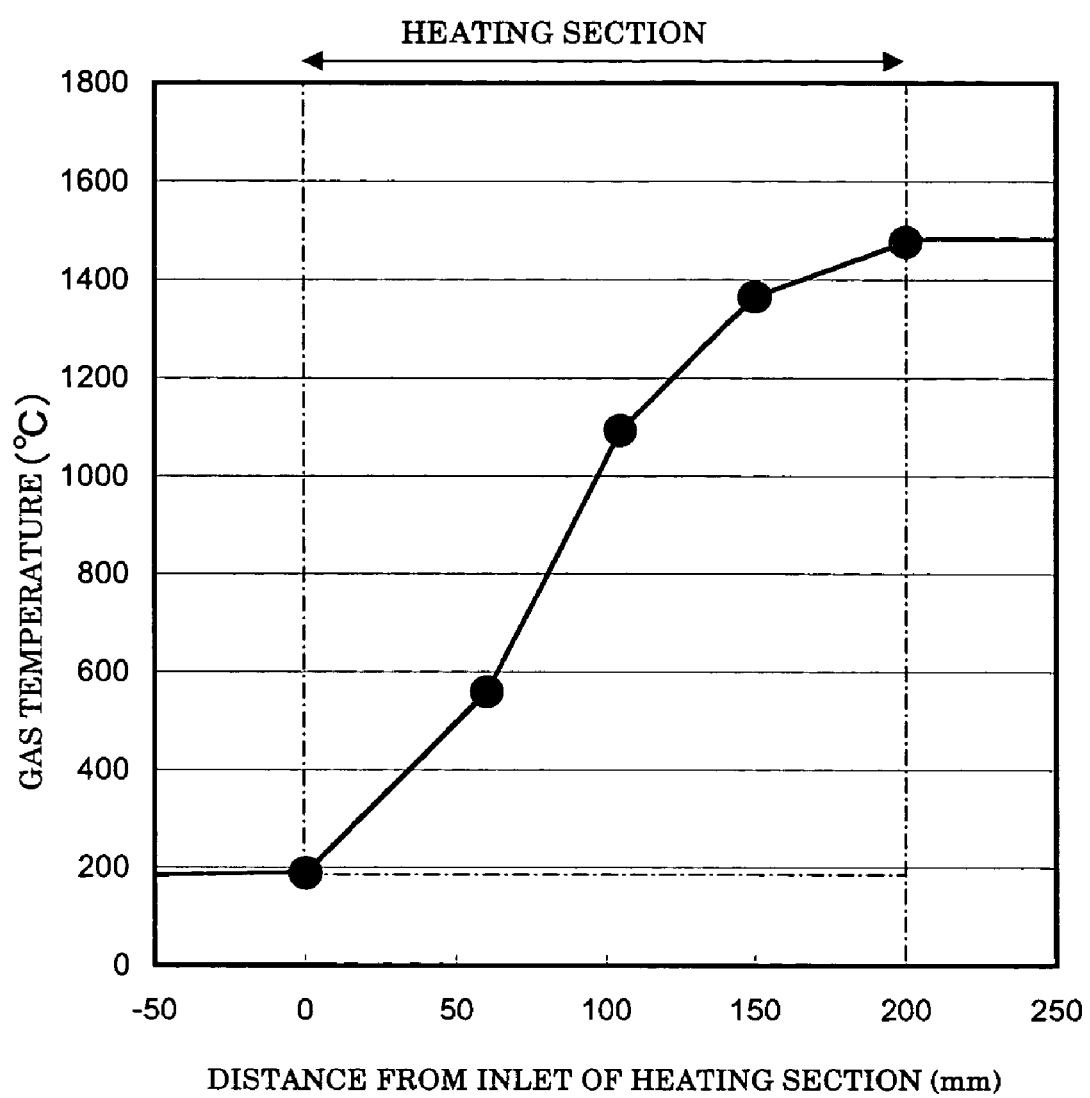
FIG. 2 is graph showing a gas temperature profile in the gas flow direction in the gas-heating section.

The gas-heating section 1 is formed of a $ZrO_2$ ceramic double-wall tube in which the outer tube has an inner diameter of 70 mm and the inner tube has an outer diameter of 20 mm. The gas-heating section has a length of 200 mm. The gas flow path provided by the space between the outer tube and the inner tube was filled with $ZrO_2$ ceramic beads serving as a radiation-conversion/heat-transfer promoter. Heating conditions of an electric furnace were adjusted such that the temperature of atmosphere gas at the outlet of the gas-heating section was controlled to about 1,500° C. In the gas flow path, five thermocouples were placed at the midpoint in the radial direction at certain intervals from the inlet of the gas-heating section, whereby the temperature profile in the gas flow direction in the gas-heating section was determined. FIG. 2 shows the results.

Next to the outlet of the gas-heating section, a $ZrO_2$ ceramic flow-limiting section 2 was provided so as to reduce the cross-sectional area through which the gas flows. The inner diameter of the inlet of the flow-limiting section 2 was 70 mm, which is equivalent to the inner diameter of the outer tube of the gas-heating section. The outlet of the flow-limiting section 2 had an inner diameter of 16 mm.

The test-piece-placing section 3 for accommodating a material test piece is formed of a $ZrO_2$ ceramic circular tube having an inner diameter of 16 mm, which is equivalent to the inner diameter of the outlet of the flow-limiting section 2. Two slits (width: about 1 mm, length: about 5 mm) were provided in the surface of the circular tube, the two slits opposing each other along the radial direction. A test piece 5 (5 mm×20 mm×1 mm) made of an alumina plate was inserted into the slits such that the test piece is retained by the $ZrO_2$ ceramic circular tube. In this case, the area of the material test piece which is in contact with the gas flow is about 16 $mm^2$ (1 mm×16 mm), and the cross-section of the gas flow path in the material-test-piece placing section has an area of about 185 $mm^2$ ($3.14 \times 8^2$ $mm^2$ − 1×16 $mm^2$). In other words, for the purpose of suppressing change in gas flow rate, the ratio of the cross-section area of the material test piece to the gas flow path area in the test-piece-placing section 3 is 10 or more.

The gas-discharging section 4 was made of a ceramic circular tube having an inner diameter of 60 mm. Similar to the gas-heating section, $ZrO_2$ ceramic beads serving as a radiation-conversion/heat-transfer promoter were charged in the discharge gas flow path to a layer thickness of about 30 mm.

The atmosphere gas which was fed to the aforementioned corrosion loss measuring apparatus was a nitrogen-steam mixture composed of saturated steam (about 90° C., about 53%) and nitrogen (about 47%), which mixture had been obtained through bubbling hot water (about 90° C.) with nitrogen. The atmosphere gas was fed to a heating conduit at 0.16 g/s and heated in the conduit to about 200° C., followed by feeding to the gas-heating section 1. As a result, at the inlet of the test-piece-placing section 3, the following conditions were attained at 1,500° C.: flow rate of about 5.4 m/s, pressure of about 0.1 MPa, and steam partial pressure of about 58 kPa.

Figure 3:
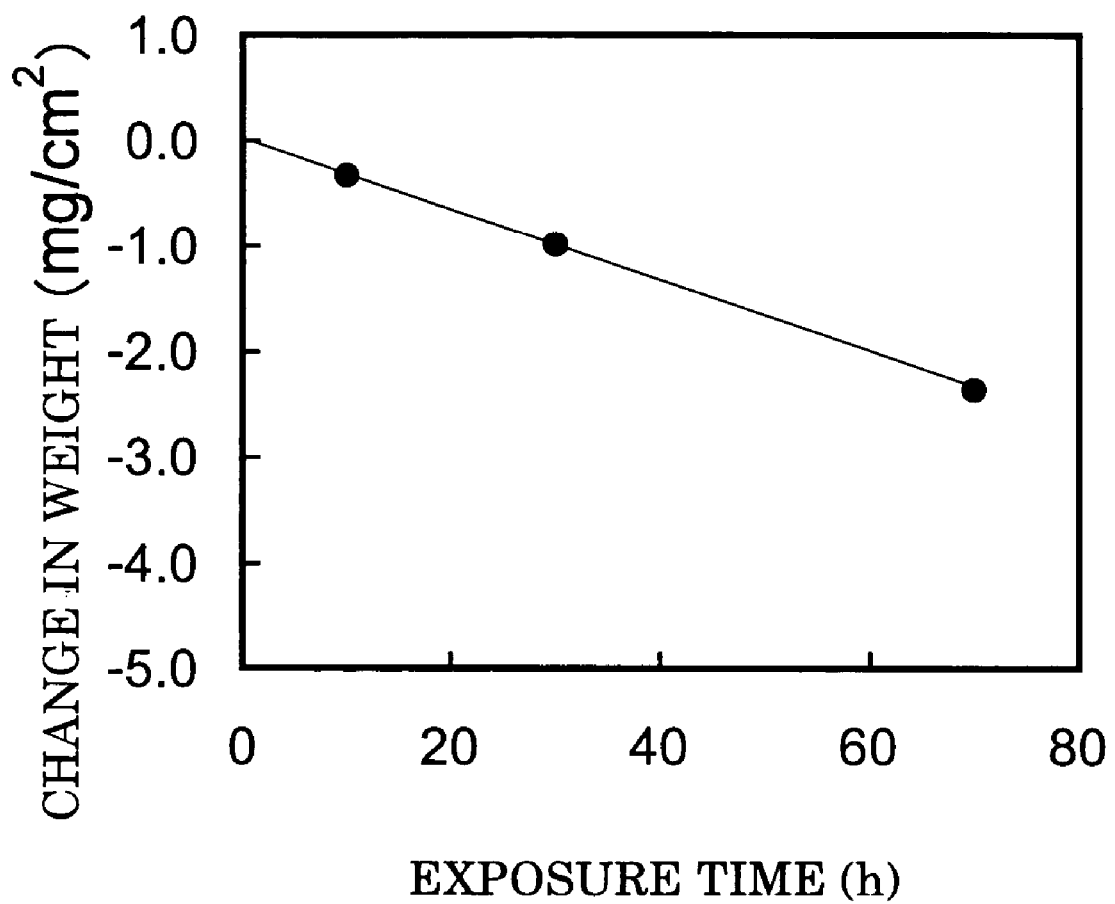
FIG. 3 is a graph showing time-dependent change in mass of an alumina test piece during the course of the corrosion loss measurement.

Time-dependent change in mass of the alumina test piece was measured during the aforementioned corrosion loss measurement. The results are shown in FIG. 3. As is clear from FIG. 3, the mass of the alumina test piece decreased with the elapse of time, indicating that the test piece underwent corrosion loss.

What is claimed is:

1. An apparatus for exposing a test piece to a corrosive gas which, during use, allows an atmosphere gas to be continuously fed into a test-piece-placing section for accommodating a material test piece, the atmosphere gas having a predetermined composition and having been heated to a predetermined temperature, wherein
the apparatus comprises a gas inlet, a gas-heating section, a flow-limiting section for gradually reducing a cross-sectional area of a gas flow path, a test-piece-placing section, a gas outlet, and a heating furnace,
the gas-heating section being situated along the gas flow path between the gas inlet and the flow-limiting section, the flow-limiting section being situated along the gas flow path between the gas-heating section and the test-piece-placing section, and the test-piece-placing section being situated along the gas flow path between the flow-limiting section and the gas outlet,
the gas-heating section, the flow-limiting section and the test-piece-placing section are included in a one-piece ceramic-made tube and the one-piece ceramic made tube is arranged in the heating furnace, and
the cross-sectional area of the gas-heating section through which the gas flows is larger than that of the test-piece-placing section.

2. The apparatus as described in claim 1, wherein the gas-heating section contains a ceramic tube having one closed end provided along the center axis of the gas flow path and in parallel to a gas flow direction, thereby forming a double-wall tube including an inner tube and an outer tube; the space between the outer tube and the inner tube serves as a gas flow path; and the gas flow path contains a ceramic-made heat-transfer promoter having gas permeability.

3. The apparatus as described in claim 1, wherein the gas-heating section contains a plurality of ceramic inner tubes, each having a closed end and containing a heating medium inserted therein, which tubes are provided in parallel to a gas flow direction in the gas flow path; and the gas flow path defined by the outer tube and the ceramic inner tubes contains a ceramic-made heat-transfer promoter having gas permeability.

4. The apparatus as described in claim 1, wherein the cross-sectional area through which the gas flows on the downstream side of a gas outlet of the test-piece-placing section is larger than that of the test-piece-placing section; the gas flow path on the downstream side of the gas outlet of the test-piece-placing section contains a ceramic-made radiation shield; and the gas-heating section, the test-piece-placing section, and the radiation shield are placed in a heating furnace.

5. The apparatus as described in claim 2, wherein the cross-sectional area through which the gas flows on the downstream side of a gas outlet of the test-piece-placing section is larger than that of the test-piece-placing section; the gas flow path on the downstream side of the gas outlet of the test-piece-placing section contains a ceramic-made radiation shield; and the gas-heating section, the test-piece-placing section, and the radiation shield are placed in a heating furnace.

6. The apparatus as described in claim 3, wherein the cross-sectional area through which the gas flows on the downstream side of a gas outlet of the test-piece-placing section is larger than that of the test-piece-placing section; the gas flow path on the downstream side of the gas outlet of the test-piece-placing section contains a ceramic-made radiation shield; and the gas-heating section, the test-piece-placing section, and the radiation shield are placed in a heating furnace.

7. The apparatus as described in claim 1, wherein the ceramic comprises zirconia, hafnia, or a mixture thereof and has a total amount of silicon dioxide and alumina as impurities of 1% or less.

8. The apparatus as described in claim 2, wherein the ceramic comprises zirconia, hafnia, or a mixture thereof and has a total amount of silicon dioxide and alumina as impurities of 1% or less.

9. The apparatus as described in claim 3, wherein the ceramic comprises zirconia, hafnia, or a mixture thereof and has a total amount of silicon dioxide and alumina as impurities of 1% or less.

10. The apparatus as described in claim 4, wherein the ceramic comprises zirconia, hafnia, or a mixture thereof and has a total amount of silicon dioxide and alumina as impurities of 1% or less.

11. The apparatus as described in claim 5, wherein the ceramic comprises zirconia, hafnia, or a mixture thereof and has a total amount of silicon dioxide and alumina as impurities of 1% or less.

12. The apparatus as described in claim 6, wherein the ceramic comprises zirconia, hafnia, or a mixture thereof and has a total amount of silicon dioxide and alumina as impurities of 1% or less.

13. The apparatus as described in claim 1, wherein a portion of each of the gas-heating section and the test-piece-placing section exposed to the atmosphere gas is formed of a ceramic material which is free from any component element of the test piece, excluding oxygen.

14. The apparatus as described in claim 2, wherein a portion of each of the gas-heating section and the test-piece-placing section exposed to the atmosphere gas is formed of a ceramic material which is free from any component element of the test piece, excluding oxygen.

15. The apparatus as described in claim 3, wherein a portion of each of the gas-heating section and the test-piece-placing section exposed to the atmosphere gas is formed of a ceramic material which is free from any component element of the test piece, excluding oxygen.

16. The apparatus as described in claim 4, wherein a portion of each of the gas-heating section and the test-piece-placing section exposed to the atmosphere gas is formed of a ceramic material which is free from any component element of the test piece, excluding oxygen.

17. The apparatus as described in claim 5, wherein a portion of each of the gas-heating section and the test-piece-placing section exposed to the atmosphere gas is formed of a ceramic material which is free from any component element of the test piece, excluding oxygen.

18. The apparatus as described in claim 6, wherein a portion of each of the gas-heating section and the test-piece-placing section exposed to the atmosphere gas is formed of a ceramic material which is free from any component element of the test piece, excluding oxygen.

* * * * *